United States Patent [19]
Van Antwerp

[11] Patent Number: 5,777,060
[45] Date of Patent: Jul. 7, 1998

[54] SILICON-CONTAINING BIOCOMPATIBLE MEMBRANES

[75] Inventor: William Peter Van Antwerp, Valencia, Calif.

[73] Assignee: Minimed, Inc., Sylmar, Calif.

[21] Appl. No.: 721,262

[22] Filed: Sep. 26, 1996

Related U.S. Application Data

[63] Continuation-in-part of Ser. No. 410,775, Mar. 27, 1995.

[51] Int. Cl.$^6$ ................................................... C08G 77/04
[52] U.S. Cl. ..................... 528/28; 128/632; 528/29; 528/41
[58] Field of Search .................... 128/632; 528/28, 528/29, 41

[56]  References Cited

U.S. PATENT DOCUMENTS

| | | |
|---|---|---|
| 4,484,987 | 11/1984 | Gough . |
| 4,759,828 | 7/1988 | Young et al. . |
| 4,816,130 | 3/1989 | Karakelle et al. . |
| 4,890,620 | 1/1990 | Gough . |
| 4,909,908 | 3/1990 | Ross et al. . |
| 5,108,819 | 4/1992 | Heller et al. . |
| 5,128,408 | 7/1992 | Tanaka et al. ............... 525/54.2 |
| 5,165,407 | 11/1992 | Wilson et al. . |
| 5,214,119 | 5/1993 | Leir et al. ......................... 528/28 |
| 5,238,732 | 8/1993 | Krishna ............................ 528/28 |
| 5,239,036 | 8/1993 | Krishna ............................ 528/28 |
| 5,239,037 | 8/1993 | Krishna ............................ 528/28 |
| 5,322,063 | 6/1994 | Allen et al. . |

FOREIGN PATENT DOCUMENTS

| | | | |
|---|---|---|---|
| 0 192 237 A1 | 12/1985 | European Pat. Off. | ........ C08F 1/40 |
| 0 390 390 | 3/1990 | European Pat. Off. | ..... G01N 27/416 |
| WO 96/15443 | 5/1996 | WIPO | ........... G01N 27/333 |
| WO 96/30431 | 10/1996 | WIPO | ............. C08G 77/26 |

OTHER PUBLICATIONS

Industrial Chemical Thesaurus, vol. 1: Chemical To Tradename Reference, 2nd ed. 1992, pp. 452 and 453.

*Primary Examiner*—Melvyn I. Marquis
*Attorney, Agent, or Firm*—Townsend and Townsend and Crew LLP

[57]  ABSTRACT

Biocompatible membranes for use with biosensors are provided. The membranes are polymers which can be prepared from (a) a diisocyanate, (b) a hydrophilic polymer, (c) a siloxane polymer having functional groups at the chain termini, and optionally, (d) a chain extender.

9 Claims, 11 Drawing Sheets

HEXAMETHYLENE DIISOCYANATE
HMI
ISOPHORONE DIISOCYANATE
IPDI
4,4'-DICYCLOHEXYLMESTHANEDIISOCYANATE
H12MDI
TRIMETHYLHEXAMETHYLENE DIISOCYANATE
TMDI
TRANS-1,4-CYCLOHEXANE DIISOCYANATE
CHDI
1,3-BIS(ISOCYANTOMETHYL)CYCLOHEXANE
CIS AND TRANS
OCNCH₂CH₂CH₂CH₂CH₂CH₂NCO
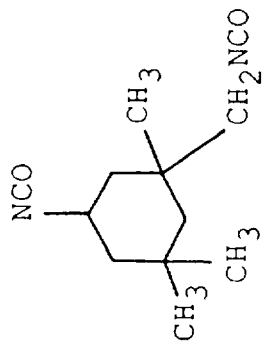
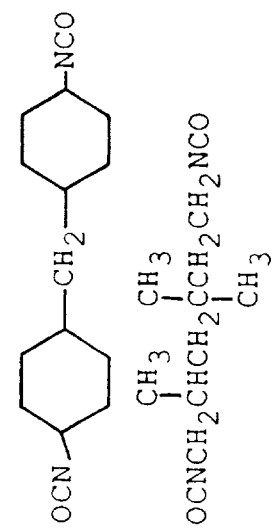
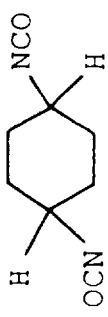
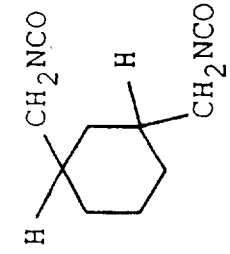
FIG. 2.

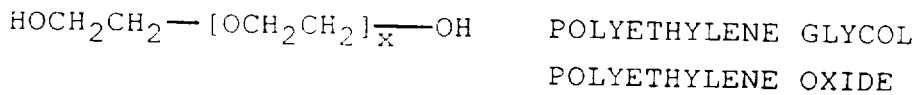 POLYETHYLENE GLYCOL
POLYETHYLENE OXIDE

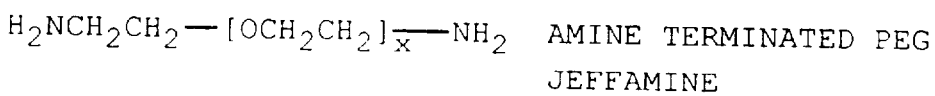 AMINE TERMINATED PEG
JEFFAMINE

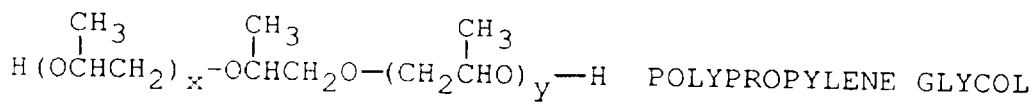 POLYPROPYLENE GLYCOL

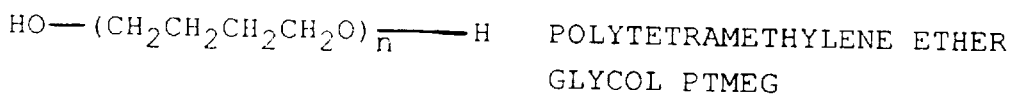 POLYTETRAMETHYLENE ETHER
GLYCOL PTMEG

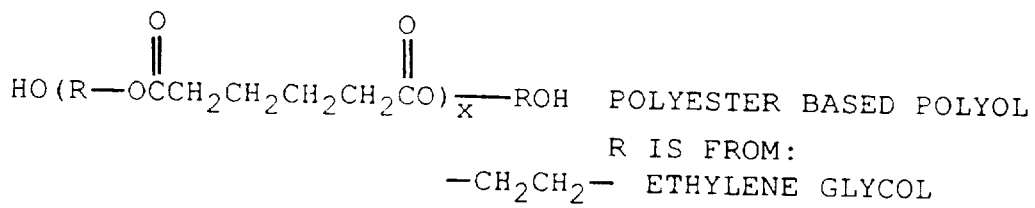 POLYESTER BASED POLYOL
R IS FROM:
—CH$_2$CH$_2$— ETHYLENE GLYCOL

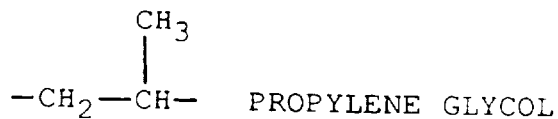 PROPYLENE GLYCOL

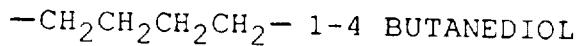 1-4 BUTANEDIOL

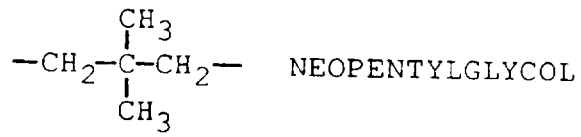 NEOPENTYLGLYCOL

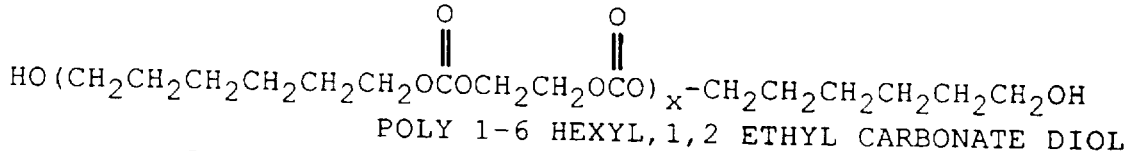
POLY 1-6 HEXYL, 1,2 ETHYL CARBONATE DIOL

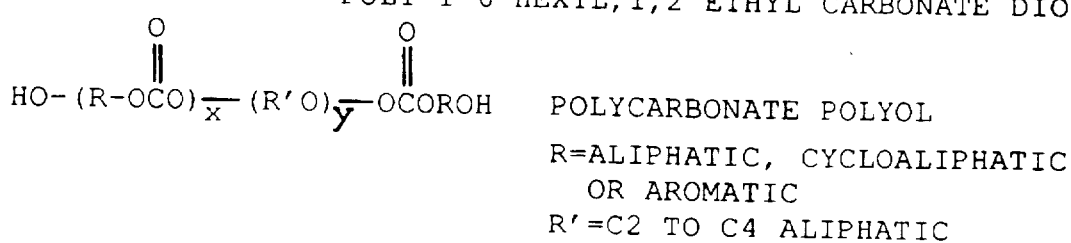 POLYCARBONATE POLYOL
R=ALIPHATIC, CYCLOALIPHATIC
  OR AROMATIC
R'=C2 TO C4 ALIPHATIC

FIG. 4.

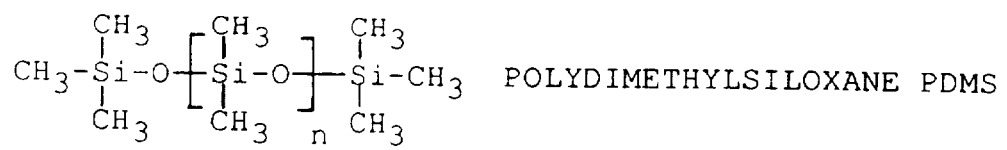
POLYDIMETHYLSILOXANE PDMS
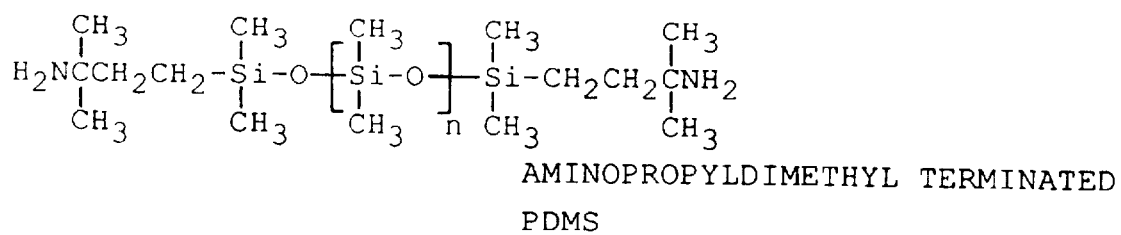
AMINOPROPYLDIMETHYL TERMINATED PDMS
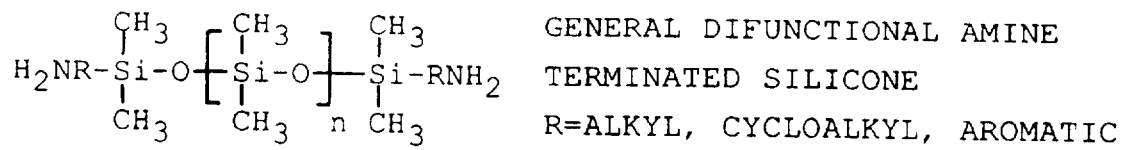
GENERAL DIFUNCTIONAL AMINE TERMINATED SILICONE
R=ALKYL, CYCLOALKYL, AROMATIC
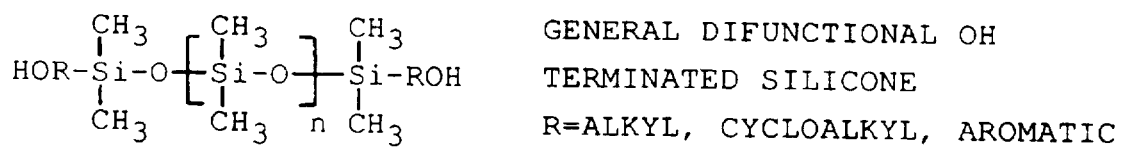
GENERAL DIFUNCTIONAL OH TERMINATED SILICONE
R=ALKYL, CYCLOALKYL, AROMATIC
*FIG. 5.*

SYNTHETIC ROUTE TO AMINO TERMINATED SILICONE POLYMER.
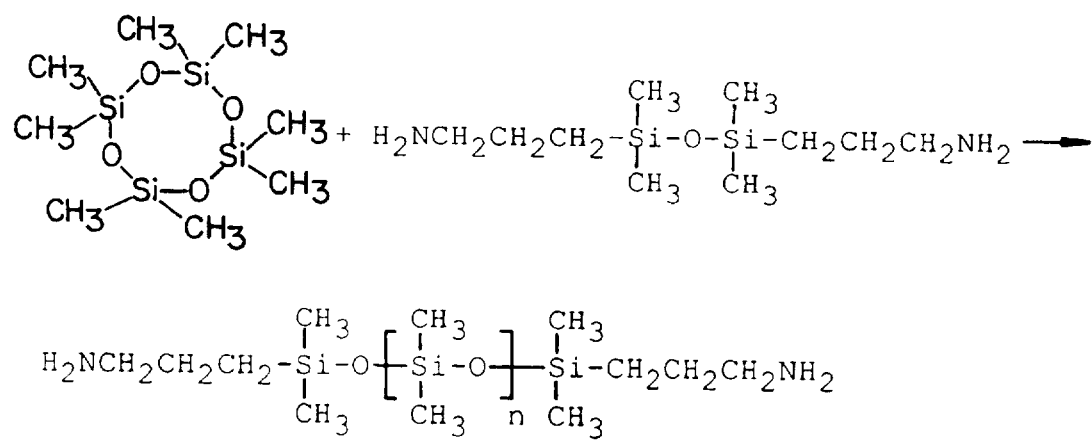
SYNTHETIC ROUTE TO OH TERMINATED SILICONE POLYMER
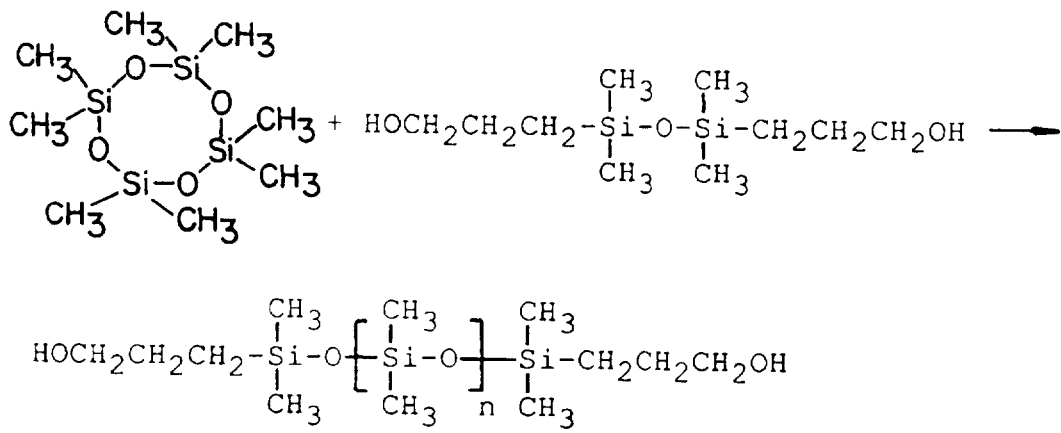
FIG. 6.

GENERAL SYNTHETIC ROUTE TO AMINO TERMINATED SILICONE POLYMER
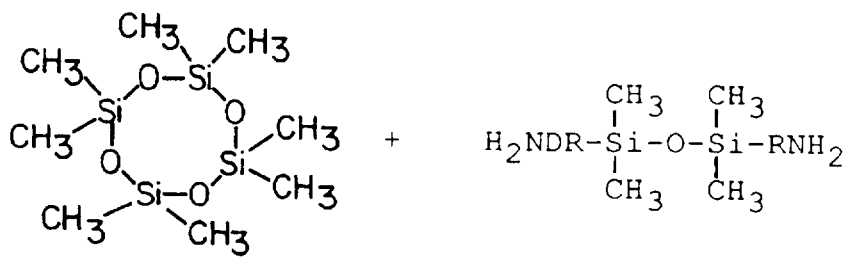
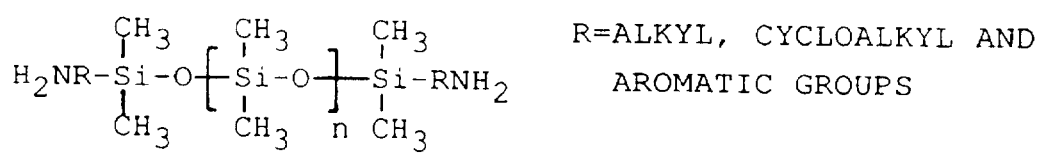
R=ALKYL, CYCLOALKYL AND AROMATIC GROUPS
GENERAL SYNTHETIC ROUTE TO OH TERMINATED SILICONE POLYMER
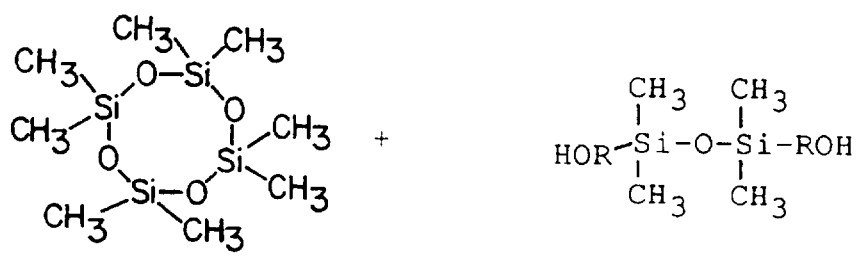
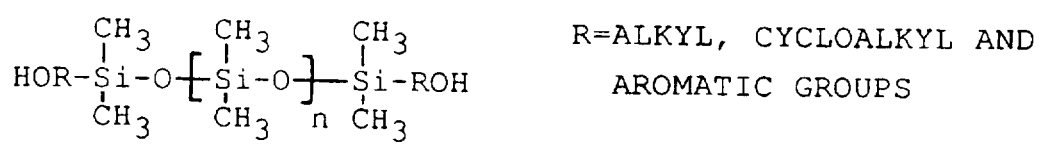
R=ALKYL, CYCLOALKYL AND AROMATIC GROUPS
*FIG. 7.*

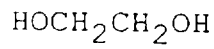 ETHYLENE GLYCOL

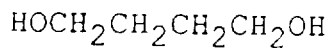 1,4-BUTANEDIOL

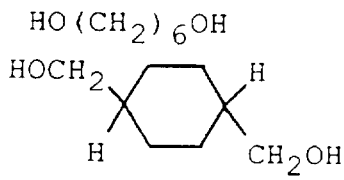 1,6-HEXANEDIOL
1,4-BIS(HYDROXYMETHYL) CYCLOHEXANE CIS AND TRANS

 P-DI(2-HYDROXYETHOXY) BENZENE HQEE

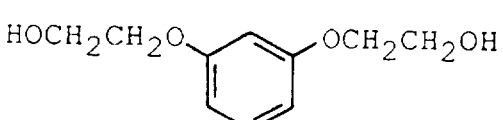 M-DI(2-HYDROXYETHOXY) BENZENE HER

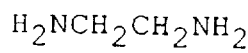 ETHYLENEDIAMINE

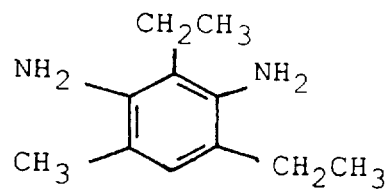 2,4-DIAMINO-3,5 DIETHYLTOLUENE ETHACURE 100 2 ISOMERS

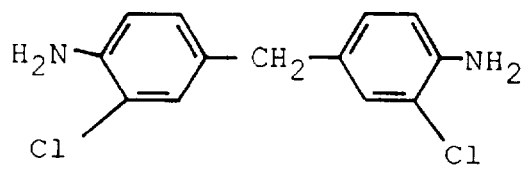 3,3'-DICHLORO-4,4' DIAMINODIPHENYLMETHANE MOCA

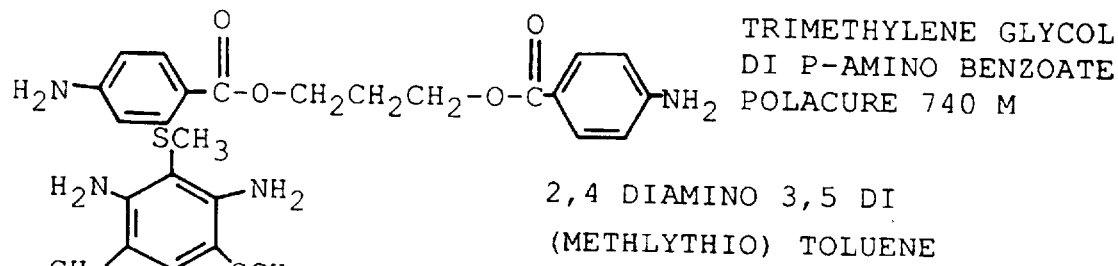

TRIMETHYLENE GLYCOL DI P-AMINO BENZOATE POLACURE 740 M

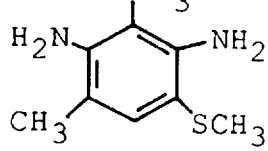 2,4 DIAMINO 3,5 DI (METHLYTHIO) TOLUENE ETHACURE 300

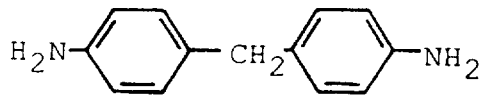 METHYLENEDIANILINE MDA

*FIG. 8.*

SILICON-CONTAINING BIOCOMPATIBLE MEMBRANES

RELATED APPLICATIONS

This application is a Continuation-in-Part of U.S. patent application Ser. No. 08/410,775, filed Mar. 27, 1995, the complete disclosure of which is incorporated herein by reference.

FIELD OF THE INVENTION

This invention lies in the field of polymer chemistry in which the polymers produced can be formed into membranes suitable for in vivo use.

BACKGROUND OF THE INVENTION

Biosensors are small devices that use biological recognition properties for selective analysis of various analytes or biomolecules. Typically, the sensor will produce a signal that is quantitatively related to the concentration of the analyte. To achieve a quantitative signal, a recognition molecule or combination of molecules is often immobilized at a suitable transducer which converts the biological recognition event into a quantitative response.

A variety of biosensors have been developed for use with numerous analytes. Electroenzymatic biosensors use enzymes to convert a concentration of analyte to an electrical signal. Immunological biosensors rely on molecular recognition of an analyte by, for example, antibodies. Chemoreceptor biosensors use chemoreceptor arrays such as those of the olfactory system or nerve fibers from the antennules of the blue crab *Callinectes sapidus* to detect the presence of amino acids in concentrations as low as $10^{-9}$M. For a review of some of the operating principles of biosensors, see Bergveld, et al., ADVANCES IN BIOSENSORS, Supplement 1, p. 31–91, Turner ed., and Collison, et al., *Anal. Chem.* 62:425–437 (1990).

Regardless of the type of biosensor, each must possess certain properties to function in vivo and provide an adequate signal. First, the elements of the biosensor must be compatible with the tissue to which it is attached and be adequately shielded from adjacent tissues such that allergic or toxic effects are not exerted. Further, the sensor should be shielded from the environment to control drift in the generated signal. Finally, the sensor should accurately measure the analyte in the presence of proteins, electrolytes and medications which may interfere.

The prototype biosensor is the amperometric glucose sensor. There are several reasons for the wide ranging interest in glucose sensors. In the healthcare arena, glucose sensors are useful for glucose monitoring of patients with diabetes mellitus. Additionally, a working glucose sensor is required for the development of a closed loop artificial pancreas with an implanted insulin pump. A commercial interest focuses on sensors that can be used to monitor fermentation reactions in the biotechnology arena. From a scientific standpoint, interest is driven by the availability of a very robust enzyme, glucose oxidase, which can be used to monitor glucose, as well as the desire to develop model sensors for a wide variety of analytes.

Any amperometric glucose sensor or any oxido-reductase enzyme that uses $O_2$ as a co-substrate and is designed for subcutaneous or intravenous use requires both an outer membrane and an anti-interference membrane. The requirement of two distinct membranes is due to the fundamental nature of the sensor as well as the environment in which the measurement is made.

A glucose sensor works according to the following chemical reaction (Equation 1):

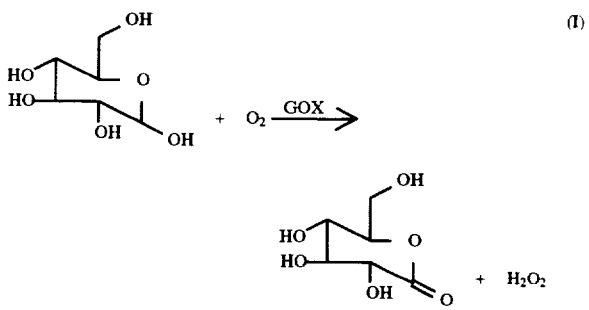

(I)

In this reaction, glucose reacts with oxygen in the presence of glucose oxidase (GOX) to form gluconolactone and hydrogen peroxide. The gluconolactone further reacts with water to hydrolyze the lactone ring and produce gluconic acid. The $H_2O_2$ reacts electrochemically as shown below (Equation 2):

$$H_2O_2 \rightarrow O_2 + 2e^- + 2H^+ \qquad (II)$$

The current measured by the sensor/potentiostat (+0.5 to +0.7 v oxidation at Pt black electrode) is due to the two electrons generated by the oxidation of the $H_2O_2$. Alternatively, one can measure the decrease in the oxygen by amperometric measurement (−0.5 to −1 V reduction at a Pt black electrode).

The stoichiometry of Equation 1 clearly demonstrates some of the problems with an implantable glucose sensor. If there is excess oxygen for Equation 1, then the $H_2O_2$ is stoichiometrically related to the amount of glucose that reacts at the enzyme. In this case, the ultimate current is also proportional to the amount of glucose that reacts with the enzyme. If there is insufficient oxygen for all of the glucose to react with the enzyme, then the current will be proportional to the oxygen concentration, not the glucose concentration. For the sensor to be a true glucose sensor, glucose must be the limiting reagent, i.e. the $O_2$ concentration must be in excess for all potential glucose concentrations. For a number of conditions, this requirement is not easily achieved. For example, the glucose concentration in the body of a diabetic patient can vary from 2 to 30 mM (millimoles per liter or 36 to 540 mg/dl), whereas the typical oxygen concentration in the tissue is 0.02 to 0.2 mM (see, Fisher, et al., *Biomed. Biochem. Acta.* 48:965–971 (1989). This ratio in the body means that the sensor would be running in the Michaelis Menten limited regime and would be very insensitive to small changes in the glucose concentration. This problem has been called the "oxygen deficit problem". Accordingly, a method or system must be devised to either increase the $O_2$ in the GOX membrane, decrease the glucose concentration, or devise a sensor that does not use $O_2$.

Several approaches to solving the deficit problem have been attempted in the past. The simplest approach is to make a membrane that is fully $O_2$ permeable, with no glucose permeability and mechanically perforate it with a small hole that allows glucose to pass. Here the differential permeability is defined by the ratio of the small hole area to the total membrane area. Two significant problems with this method are first that reproducibly making small holes is difficult and second and more serious, the $O_2$ permeability is a strong function of the thickness of the membrane and thickness is difficult to control in mass production. Microporous membranes (U.S. Pat. No. 4,759,828 to Young et al., incorporated herein by reference) have also been tried with limited success. Another problem with both the perforated membrane approach and the microporous membrane approach is that the sensor electrodes and the enzyme layer are exposed to body fluids. Body fluids contain proteins that coat the electrodes leading to decreased sensitivity of the sensor and enzymes (proteases) that can digest or degrade the sensor active enzyme.

Another approach to the oxygen deficit problem is described by Gough (U.S. Pat. No. 4,484,987, incorporated herein by reference). The approach uses a combination membrane with discrete domains of a hydrophilic material embedded in a hydrophobic membrane. In this case, the membrane is not homogenous and manufacturing reproducibility is difficult. Physical properties of the membrane are also compromised. In a similar manner, Gough (U.S. Pat. No. 4,890,620, incorporated herein by reference) describes a "two dimensional" system where glucose diffusion is limited to one dimension while the oxygen diffusion is from both dimensions. This sensor is extremely complicated and manufacturing on a large scale is expected to be difficult.

Several other groups have used a homogenous membrane of a relatively hydrophobic polyurethane and reported good results. See, for example, Shaw, et al., *Biosensors and Bioelectronics*, 6:401–406 (1991); Bindra, et al., *Anal. Chem.* 63:1692 (1991); and Schichiri, et al., *Horm. Metab. Resl. Suppl. Ser.*, 20:17 (1988). In classical diffusion experiments with these membranes, however, the glucose diffusion is extremely small. It is believed that the ability of these polyurethane layers to allow glucose diffusion is due to micro cracks or micro holes in these materials when applied as membranes.

Still others have developed homogeneous membranes with both hydrophilic and hydrophobic regions to circumvent the oxygen deficit problem. See, Allen et al., U.S. Pat. Nos. 5,284,140 and 5,322,063, the disclosures of each being incorporated herein by reference. These patents describe acrylic and polyurethane systems, respectively. Both of the membranes have hydrophilic and hydrophobic moieties in the molecule leading to limited control of oxygen and glucose permeabilities.

The key to stable, high sensitivity enzyme biosensors is that the sensor output must be limited only by the analyte of interest, not by any co-substrates or kinetically controlled parameters such as diffusion. In order to maximize the output current (Equation 2) of the biosensor, oxygen diffusion should be as large as possible while maintaining oxygen excess at the reaction surface. Since the normal concentration of $O_2$ in the subcutaneous tissue is quite low, maximization of the $O_2$ diffusion coefficient is desirable.

The membrane systems described in the literature as cited above attempt only to circumvent the oxygen deficit problem by reducing the amount of glucose diffusion to the working electrode of the biosensor. There is a need for the membrane to have physical stability and strength, adhesion to the substrate, processibility (ability to be synthesized/manufactured in reasonable quantities and at reasonable prices), biocompatibility, ability to be cut by laser ablation (or some other large scale processing method), and compatibility with the enzyme as deposited on the sensor. The present invention fulfills these needs and provides other related advantages.

SUMMARY OF THE INVENTION

The present invention provides compositions which are biocompatible and suitable for coating a biosensor. The compositions are polymers which are formed into membranes and can be prepared from:

(a) a diisocyanate, (b) a hydrophilic polymer which is a hydrophilic diol, a hydrophilic diamine, or a combination thereof, (c) a siloxane polymer having functional groups at the chain termini, and optionally, (d) a chain extender.

The membranes prepared from the above components will have a glucose diffusion coefficient of from about $1\times10^{-9}$ $cm^2/sec$ to about $200\times10^{-9}$ $cm^2/sec$, a water pickup of at least about 25% and a ratio of $D_{oxygen}/D_{glucose}$ of about 5 to about 200.

In certain preferred embodiments, the functional groups present in the siloxane polymer are amino, hydroxyl or carboxylic acid, more preferably amino or hydroxyl groups. In other preferred embodiments, the hydrophilic polymer is a poly(ethylene)glycol which is PEG 200, PEG 400 or PEG 600. In still other preferred embodiments the diisocyanate is a isophorone diisocyanate, 1,6-hexamethylene diisocyanate or 4,4'-methylenebis(cyclohexyl isocyanate) and the chain extender is an alkylene diol, an alkylene diamine, an aminoalkanol or a combinations thereof.

In particularly preferred embodiments, the diisocyanate is 1,6-hexamethylene diisocyanate, the hydrophilic polymer is PEG 400 or PEG 600 and is present in an amount of about 17 to about 32 mol % (relative to all reactants), and the siloxane polymer is aminopropyl polysiloxane having a molecular weight of about 2000 to about 4000 and is present in an amount of about 17 to about 32 mol % (relative to all reactants).

The present invention further provides an implantable biosensor for measuring the reaction of an analyte, preferably glucose, and oxygen, the biosensor having a biocompatible membrane as described above.

BRIEF DESCRIPTION OF THE DRAWINGS

FIGS. 2 and 3 provide the structures of certain aliphatic and aromatic diisocyanates which are useful in forming the membranes described below.

FIG. 4 provides the structures of a number of hydrophilic polymers including poly(alkylene) glycols and diamino poly (alkylene oxides) which are used in polymers described below.

FIG. 5 provides the structures of certain silicones which are useful in forming the membranes described below.

FIGS. 6 and 7 provides synthetic procedures for the preparation of some silicone polymers used in the present invention.

FIG. 8 provides the structures of some chain extenders which are useful in the present compositions. This include aliphatic diols, diamines and alkanolamines and further include some aromatic diols and diamines.

FIG. 10 illustrates portions of a glucose sensor which can be coated with a membrane of the present invention.

DETAILED DESCRIPTION OF THE INVENTION

The following abbreviations are used herein: dl, deciliter; DEG, diethylene glycol; DMF, dimethyl formamide; PBS, phosphate buffered saline; THF, tetrahydrofuran; DI, deionized; PEG, poly(ethylene)glycol; HDI, 1,6-hexane diisocyanate (1,6hexamethylene diisocyanate); TMDI, 2,2,4,4-tetramethyl-1,6-hexane diisocyanate and 2,4,4-trimethyl-1,6-hexane diisocyanate; CHDI, 1,4-cyclohexane diisocyanate; BDI, 1,4cyclohexane bis(methylene isocyanate); $H_6XDI$, 1,3-cyclohexane bis(methylene isocyanate) or hexahydro metaxylene diisocyanate; IPDI, isophorone diisocyanate; and $H_{12}MDI$, 4,4'dicyclohexylmethane diisocyanate.

As used herein, the term "polyurethane/polyurea" refers to a polymer containing urethane linkages, urea linkages or combinations thereof. Typically, such polymers are formed by combining diisocyanates with alcohols and/or amines. For example, combining isophorone diisocyanate with PEG 600 and aminopropyl polysiloxane under polymerizing conditions provides a polyurethane/polyurea composition having both urethane (carbamate) linkages and urea linkages.

Biocompatible Membranes

As noted above, requirements for a glucose sensor intended for in vivo use is that the supply of oxygen in the vicinity of the sensing element not be depleted. Additionally, the glucose should diffuse to the sensor at a controlled rate. This does not mean that a glucose sensor membrane need have an extremely high permeability to oxygen. Instead, the membrane should control the relative rates of diffusion of oxygen and glucose to the sensor so that the local concentration of oxygen is not depleted. Additionally, the glucose sensors intended for in vivo use must also be biocompatible with the body, and they must be able to function in an environment in which acids are present as well as proteins which can interfere with a sensor. Thus, the enzyme(s) used in such sensors must be protected from degradation or denaturation, while the elements of such sensors must be protected from molecules which would foul the sensors or their accuracy will decrease over time.

In one aspect, the present invention provides a biocompatible membrane formed from a reaction mixture of:

(a) a diisocyanate, said diisocyanate comprising about 50 mol % of the reactants in said mixture;

(b) a hydrophilic polymer which is a member selected from the group consisting of a hydrophilic diol, a hydrophilic diamine and combinations thereof; and (c) a silicone polymer having functional groups at the chain termini. Optionally, the reaction mixture will contain a chain extender. The membrane formed using the polymerized mixture of the above components will have a glucose diffusion coefficient of from about 1 to about 200–$10^{-9}$ cm$^2$/sec, a water pickup of at least 25% and a ratio of $D_{oxygen}/D_{glucose}$ of from about 5 to about 200.

Figure 1:
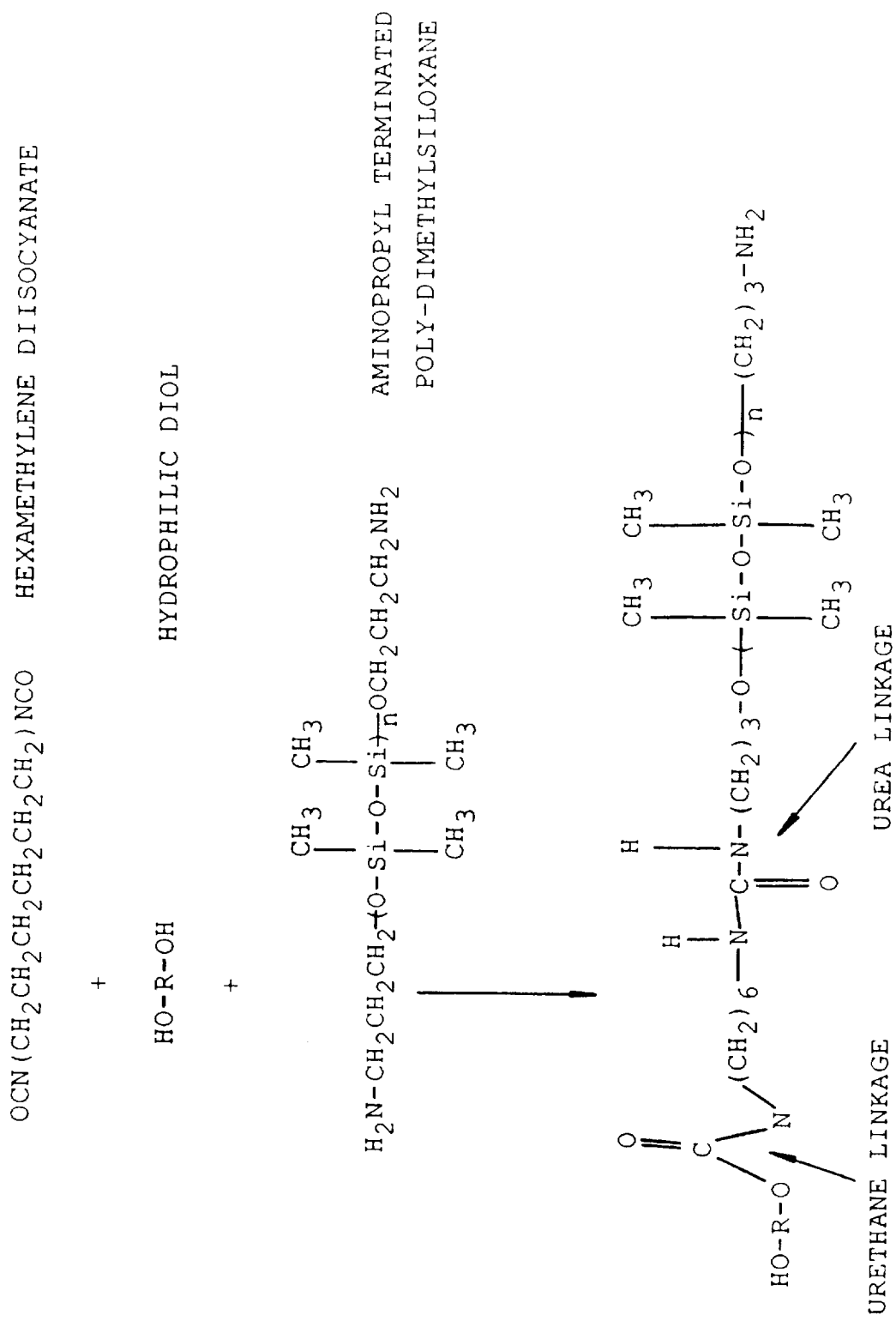
FIG. 1 illustrates polymerization reactions of a diisocyanate with a poly(alkylene) glycol or a diamino poly (alkylene oxide) which results in a polyurethane or polyurea, respectively.

Depending on the selection of components, the polymer used in forming the biocompatible membranes will be a polyurea, a polyurethane or a polyurethane/polyurea combination. FIG. 1 illustrates some of the polymerization reactions which result in the compositions of the present invention.

Membrane components

The homogeneous membranes of the invention are prepared from biologically acceptable polymers whose hydrophobic/hydrophilic balance can be varied over a wide range to control the ratio of the diffusion coefficient of oxygen to that of glucose, and to match this ratio to the design requirements of electrochemical glucose sensors intended for in vivo use. Such membranes can be prepared by conventional methods by the polymerization of monomers and polymers noted above. The resulting polymers are soluble in solvents such as acetone or ethanol and may be formed as a membrane from solution by dip, spray or spin coating.

Figure 3:
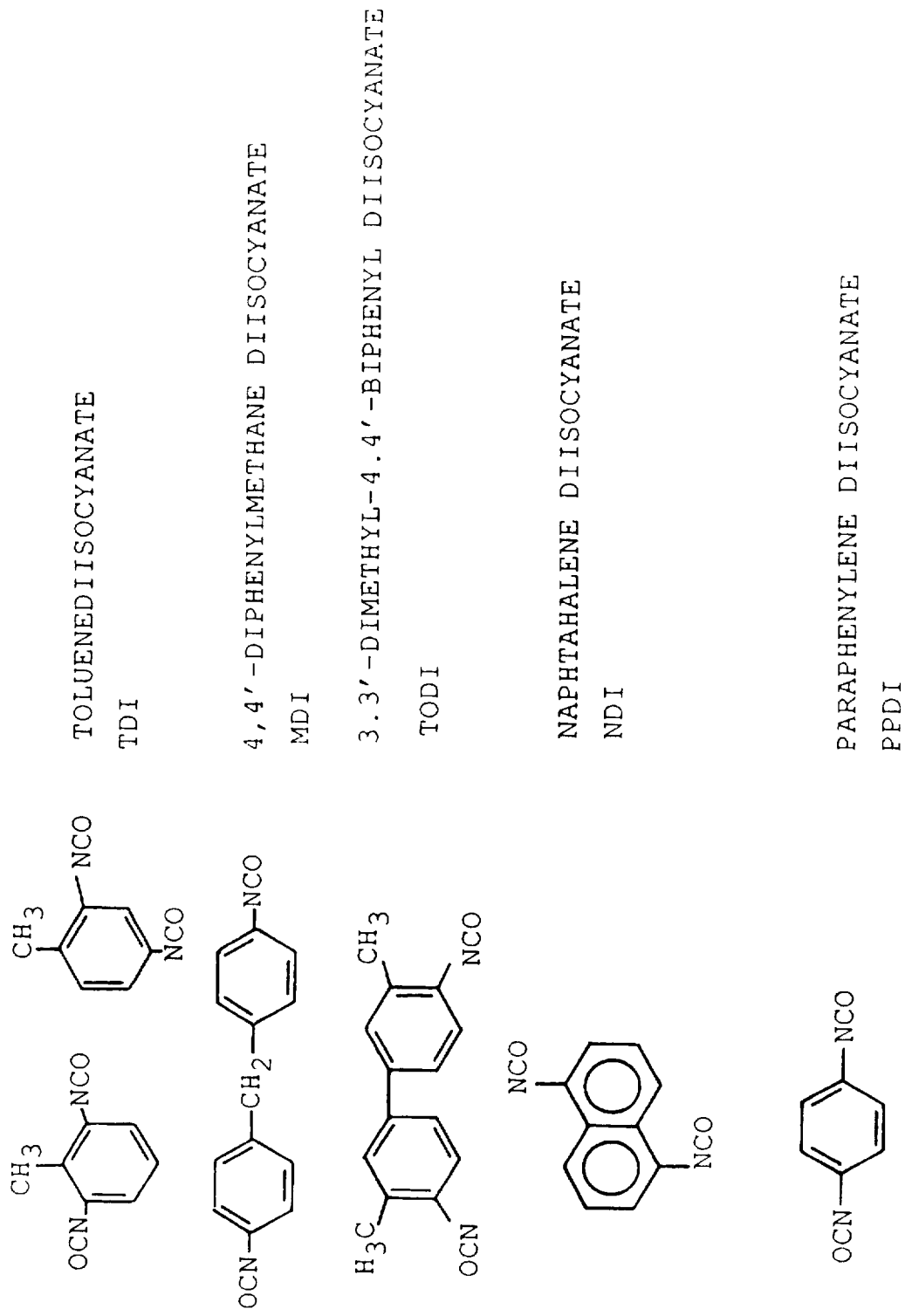

The diisocyanates which are useful in this aspect of the invention are those which are typically those which are used in the preparation of biocompatible polyurethanes. Such diisocyanates are described in detail in Szycher, SEMINAR ON ADVANCES IN MEDICAL GRADE POLYURETHANES, Technomic Publishing, (1995) and include both aromatic and aliphatic diisocyanates (see FIGS. 2 and 3). Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6hexamethylene diisocyanate (HDI), trimethylhexamethylene diisocyanate (TMDI), trans1,4-cyclohexane diisocyanate (CHDI), 1,4-cyclohexane bis(methylene isocyanate) (BDI), 1,3-cyclohexane bis(methylene isocyanate) ($H_6XDI$), isophorone diisocyanate (IPDI) and 4,4'-methylenebis(cyclohexyl isocyanate) ($H_2MDI$). In preferred embodiments, the diisocyanate is isophorone diisocyanate, 1,6-hexamethylene diisocyanate, or 4,4'methylenebis (cyclohexyl isocyanate). A number of these diisocyanates are available from commercial sources such as Aldrich Chemical Company (Milwaukee, Wis., USA) or can be readily prepared by standard synthetic methods using literature procedures.

The quantity of diisocyanate used in the reaction mixture for the present compositions is typically about 50 mol % relative to the combination of the remaining reactants. More particularly, the quantity of diisocyanate employed in the preparation of the present compositions will be sufficient to provide at least about 100% of the —NCO groups necessary to react with the hydroxyl or amino groups of the remaining reactants. For example, a polymer which is prepared using x moles of diisocyanate, will use a moles of a hydrophilic polymer (diol, diamine or combination), b moles of a silicone polymer having functionalized termini, and c moles of a chain extender, such that x=a+b+c, with the understanding that c can be zero.

A second reactant used in the preparation of the biocompatible membranes described herein is a hydrophilic polymer. The hydrophilic polymer can be a hydrophilic diol, a hydrophilic diamine or a combination thereof. The hydrophilic diol can be a poly(alkylene)glycol, a polyester-based polyol, or a polycarbonate polyol (see FIG. 4). As used herein, the term "poly(alkylene)glycol" refers to polymers of lower alkylene glycols such as poly(ethylene)glycol, poly(propylene)glycol and polytetramethylene ether glycol (PTMEG). The term "polyester-based polyol" refers to a polymer as depicted in FIG. 4 in which the R group is a lower alkylene group such as ethylene, 1,3-propylene, 1,2-propylene, 1,4-butylene,2,2-dimethyl-1,3-propylene, and the like. One of skill in the art will also understand that the diester portion of the polymer can also vary from the six-carbon diacid shown. For example, while FIG. 4 illustrates an adipic acid component, the present invention also contemplates the use of succinic acid esters, glutaric acid esters and the like. The term "polycarbonate polyol" refers those polymers having hydroxyl functionality at the chain termini and ether and carbonate functionality within the polymer chain (see FIG. 4). The alkyl portion of the polymer will typically be composed of C2 to C4 aliphatic radicals, or in some embodiments, longer chain aliphatic radicals, cycloaliphatic radicals or aromatic radicals. The term "hydrophilic diamines" refers to any of the above hydrophilic diols in which the terminal hydroxyl groups have been replaced by reactive amine groups or in which the terminal hydroxyl groups have been derivatized to produce an extended chain having terminal amine groups. For example, a preferred hydrophilic diamine is a "diamino poly(oxyalkylene)" which is poly(alkylene)glycol in which the terminal hydroxyl groups are replaced with amino groups. The term "diamino poly(oxyalkylene)" also refers to poly(alkylene)glycols which have aminoalkyl ether groups at the chain termini. One example of a suitable diamino poly(oxyalkylene) is poly(propylene glycol)bis(2-aminopropyl ether). A number of the above polymers can be obtained from Aldrich Chemical Company. Alternatively, literature methods can be employed for their synthesis.

The amount of hydrophilic polymer which is used in the present compositions will typically be about 10% to about 80% by mole relative to the diisocyanate which is used. Preferably, the amount is from about 20% to about 60% by mole relative to the diisocyanate. When lower amounts of hydrophilic polymer are used, it is preferable to include a chain extender (see below).

Silicone polymers which are useful in the present invention are typically linear, have excellent oxygen permeability and essentially no glucose permeability. Preferably, the silicone polymer is a polydimethylsiloxane having two reactive functional groups (i.e. a functionality of 2). The functional groups can be, for example, hydroxyl groups, amino groups or carboxylic acid groups, but are preferably hydroxyl or amino groups (see FIG. 5). In some embodiments, combinations of silicone polymers can be used in which a first portion comprises hydroxyl groups and a second portion comprises amino groups. Preferably, the functional groups are positioned at the chain termini of the silicone polymer. A number of suitable silicone polymers are commercially available from such sources as Dow Chemical Company (Midland, Mich., USA) and General Electric Company (Silicones Division, Schenectady, N.Y., USA). Still others can be prepared by general synthetic methods as illustrated in FIGS. 6 and 7, beginning with commercially available siloxanes (United Chemical Technologies, Bristol, Pa., USA). For use in the present invention, the silicone polymers will preferably be those having a molecular weight of from about 400 to about 10,000, more preferably those having a molecular weight of from about 2000 to about 4000. The amount of silicone polymer which is incorporated into the reaction mixture will depend on the desired characteristics of the resulting polymer from which the biocompatible membrane are formed. For those compositions in which a lower glucose penetration is desired, a larger amount of silicone polymer can be employed. Alternatively, for compositions in which a higher glucose penetration is desired, smaller amounts of silicone polymer can be employed. Typically, for a glucose sensor, the amount of siloxane polymer will be from 10% to 90% by mole relative to the diisocyanate. Preferably, the amount is from about 20% to 60% by mole relative to the diisocyanate.

In one group of embodiments, the reaction mixture for the preparation of biocompatible membranes will also contain a chain extender which is an aliphatic or aromatic diol, an aliphatic or aromatic diamine, alkanolamine, or combinations thereof (see FIG. 8). Examples of suitable aliphatic chain extenders include ethylene glycol, propylene glycol, 1,4-butanediol, 1,6-hexanediol, ethanolamine, ethylene diamine, butane diamine, 1,4-cyclohexanedimethanol. Aromatic chain extenders include, for example, para-di(2-hydroxyethoxy)benzene, meta-di(2-hydroxyethoxy)benzene, Ethacure 100® (a mixture of two isomers of 2,4-diamino-3,5-diethyltoluene), Ethacure 300® (2,4-diamino-3,5-di(methylthio)toluene), 3,3'-dichloro-4,4'diaminodiphenylmethane, Polacure® 740M (trimethylene glycol bis(para-aminobenzoate)ester), and methylenedianiline. Incorporation of one or more of the above chain extenders typically provides the resulting biocompatible membrane with additional physical strength, but does not substantially increase the glucose permeability of the polymer. Preferably, a chain extender is used when lower (i.e., 10–40 mol %) amounts of hydrophilic polymers are used. In particularly preferred compositions, the chain extender is diethylene glycol which is present in from about 40% to 60% by mole relative to the diisocyanate.

Membrane preparation

Polymerization of the above reactants can be carried out in bulk or in a solvent system. Use of a catalyst is preferred, though not required. Suitable catalysts include dibutyltin bis(2-ethylhexanoate), dibutyltin diacetate, triethylamine and combinations thereof. Preferably dibutyltin bis(2-ethylhexanoate is used as the catalyst. Bulk polymerization is typically carried out at an initial temperature of about 25° C. (ambient temperature) to about 50° C., in order to insure adequate mixing of the reactants. Upon mixing of the reactants, an exotherm is typically observed, with the temperature rising to about 90°–120° C. After the initial exotherm, the reaction flask can be heated at from 75° C. to 125° C., with 90° C. to 100° C. being a preferred temperature range. Heating is usually carried out for one to two hours. Solution polymerization can be carried out in a similar manner. Solvents which are suitable for solution polymerization include dimethylformamide, dimethyl sulfoxide, dimethylacetamide, halogenated solvents such as 1,2,3-trichloropropane, and ketones such as 4-methyl-2-pentanone. Preferably, THF is used as the solvent. When polymerization is carried out in a solvent, heating of the reaction mixture is typically carried out for three to four hours.

Polymers prepared by bulk polymerization are typically dissolved in dimethylformamide and precipitated from water. Polymers prepared in solvents that are not miscible with water can be isolated by vacuum stripping of the solvent. These polymers are then dissolved in dimethylformamide and precipitated from water. After thoroughly washing with water, the polymers can be dried in vacuo at about 50° C. to constant weight.

Preparation of the membranes can be completed by dissolving the dried polymer in a suitable solvent and cast a film onto a glass plate. The selection of a suitable solvent for casting will typically depend on the particular polymer as well as the volatility of the solvent. Preferably, the solvent is THF, $CHCl_3$, $CH_2Cl_2$, DMF or combinations thereof. More preferably, the solvent is THF or $DMF/CH_2Cl_2$ (2/98 volume %), the solvent is removed from the films, the resulting membranes are hydrated fully, their thicknesses measured and water pickup is determined. Membranes which are useful in the present invention will typically have a water pickup of about 20 to about 100%, preferably 30 to about 90%, and more preferably 40 to about 80%, by weight.

Oxygen and glucose diffusion coefficients can also be determined for the membranes of the present invention.

Methods for determining diffusion coefficients are known to those of skill in the art, and examples are provided below. The biocompatible membranes described herein will preferably have a oxygen diffusion coefficient ($D_{oxygen}$) of about $0.1 \times 10^{-6}$ cm$^2$/sec to about $2.0 \times 10^{-6}$ cm$^2$/sec and a glucose diffusion coefficient ($D_{glucose}$) of about $1 \times 10^{-9}$ cm$^2$/sec to about $500 \times 10^{-9}$ cm$^2$/sec. More preferably, the glucose diffusion coefficient is about $10 \times 10^{-9}$ cm$^2$/sec to about $200 \times 10^{-9}$ cm$^2$/sec.

From the above description, it will be apparent to one of skill in the art that the discovery underlying the present invention is the use of silicon-containing polymers, such as siloxanes, in the formation of biocompatible membranes. The silicon-containing polymers are used in conjunction with (covalently attached to) hydrophilic polymers for the preparation of membranes in which the movement of analytes and reactive species (e.g., oxygen and glucose) can be controlled by varying the amounts of each component. The membranes produced from these components are homogeneous and are useful for coating a number of biosensors and devices designed for subcutaneous implantation.

Membrane-Coated Biosensors

Glucose sensors which utilize, for example, glucose oxidase to effect a reaction of glucose and oxygen are known in the art, and are within the skill in the art to fabricate. See, for example, U.S. Pat. Nos. 5,165,407, 4,890,620, 5,390,671 and 5,391,250, the disclosures of each being incorporated herein by reference. The present invention depends not on the configuration of the biosensor, but rather on the use of the inventive membranes to cover or encapsulate the sensor elements.

In particular, the biocompatible membranes of the present invention are useful with a variety of biosensors for which it is advantageous to control diffusion of the analytes/reactants to the sensing elements. Various such biosensors are well known in the art. For example, other sensors for monitoring glucose concentration of diabetics are described in Shichiri, et al.: "In Vivo Characteristics of Needle-Type Glucose Sensor-Measurements of Subcutaneous Glucose Concentrations in Human Volunteers," *Horm. Metab. Res.*, Suppl. Ser. 20:17-20 (1988); Bruckel, et al.: "In Vivo Measurement of Subcutaneous Glucose Concentrations with an Enzymatic Glucose Sensor and a Wick Method," *Klin. Wochenschr.* 67:491-495 (1989); and Pickup, et al.: "In Vivo Molecular Sensing in Diabetes Mellitus: An Implantable Glucose Sensor with Direct Electron Transfer," *Diabetologia* 32:213-217 (1989).

The following examples are offered by way of illustration and are not meant to limit the scope of the invention.

EXAMPLES

The materials used in the examples were obtained from commercial sources.

General Methods (a) Membrane Preparation

Membranes were prepared by casting films from a suitable solvent onto glass plates using a parallel arm Gardner knife (Gardner Labs). The solvent chosen will depend on the particular chemical structure of the polymer. Typically, THF or DMF/CH$_2$Cl$_2$ (2/98 vol %) are used although chloroform is also useful as it is readily volatile. After removal of the solvent, the dried membranes were hydrated with deionized water for 30-60 minutes. The membranes were then removed and transferred to a Mylar® support sheet. Wet film thicknesses were measured with a micrometer before removal from the support. Films were also cast from solution onto filtration membranes of known thickness. For the measurements provided below, it was assumed that the membrane material completely filled the pores of the filtration membranes and that the thickness of the filtration media is the thickness of the membrane.

(b) Diffusion constants Diffusion constants were measured in a standard permeability cell (Crown Glass Co., Inc.) maintained at 37° C., using Fick's relationship:

$$J = -D \, dC/dx$$

where J is total flux, D is the diffusion constant of the analyte of interest, and dC/dx is the concentration gradient across the membrane. The diffusion coefficient is a physical property of both the analyte of interest and the material in which it is diffusing. Thus, D is a property of the system under evaluation.

Oxygen diffusion constants ($D_o$) were determined by securing the membrane with two rubber gaskets between the two halves of a diffusion cell maintained at 37° C., and clamping the two halves together. Each side of the cell was filled with phosphate buffered saline (PBS, 0.15M NaCl, 0.05M phosphate, pH 7.4). One side was saturated with HPLC grade helium while the other side was saturated with room air (assumed 20% O$_2$). A calibrated oxygen electrode (Microelectrodes, Inc.) was placed in each cell. The oxygen electrode outputs were connected to a microcomputer-controlled data acquisition system and the oxygen concentration from both cells was recorded as a function of time. The curves of concentration vs. time were plotted and the diffusion coefficients were calculated using the entire curve. Curve fits generally had correlation coefficients (R$^2$) of greater than 0.95.

Glucose diffusion constants ($D_G$) were determined as above except that one half of the cell was filled with phosphate buffered saline containing 400 mg/dl of glucose. The concentration of glucose in each half of the cell was measured at 5 minute intervals until equilibrium was achieved using a YSI glucose analyzer. As above, the curves of concentration vs. time were plotted and the diffusion coefficient was calculated.

(c) Water pickup Water pickup was determined gravimetrically at room temperature on films which were less than 0.5 mm thick. After evaporation of the casting solvent, films were dried to constant weight at 50° C. in vacuo, weighed, immersed in deionized water for 24 hours, removed and blotted with filter paper, and weighed. Percent water pickup was determined from the formula:

$$\% \text{ Pickup} = (W_w - W_d)/W_d \times 100$$

where $W_w$ is the weight of the swollen film and $W_d$ is the weight of the dry film.

EXAMPLE 1

This example illustrates a bulk polymerization method of polymer formation carried out with isophorone diisocyanate, PEG 600, diethylene glycol and aminopropyl terminated polydimethyl siloxane.

Isophorone diisocyanate (4.44 g, 20 mmol, 100 mol %) was dried over molecular sieves and transferred to a 100 mL round bottom flask fitted with a nitrogen purge line and a reflux condenser. PEG 600 (2.40 g, 4.0 mmol, 20 mol %), diethylene glycol (1.06 g, 10 mmol, 50 mol %) and aminopropyl terminated polydimethylsiloxane (15 g, 6.0 mmol, 30 mol %, based on a 2500 average molecular weight) were added to the flask. Heating was initiated using a heating mantle until a temperature of 50° C. was obtained. Dibutyltin bis(2-ethylhexanoate) (15 mg) was added and the temperature increased to about 95° C. The solution was continuously stirred at a temperature of 65° C. for a period of 4 hr during which time the mixture became increasingly viscous. The resulting polymer was dissolved in 50 mL of hot THF and cooled. After cooling, the solution was poured into 5 L of stirring DI water. The precipitated polymer was torn into small pieces and dried at 50° C. until a constant weight was achieved.

EXAMPLE 2

This example illustrates a solution polymerization method using 1,6-hexamethylene diisocyanate, PEG 200 and aminopropyl terminated polydimethylsiloxane.

Dried 1,6-hexamethylene diisocyanate (1.34 g, 8 mmol, 100 mol %) was added to a 100 mL 3-neck flask containing 20 mL of dry THF. PEG 200 (0.8 g, 4.0 mmol, 50 mol %) was added with stirring followed by addition of aminopropyl terminated polydimethylsiloxane (10 g, 4.0 mmol, 50 mol %). The resulting solution was warmed to 50° C. and dibutyltin bis(2-ethylhexanoate) (about 15 mg) was added. After an initial temperature rise to 83° C., the mixture was warmed and held at 70° C. for 12 hr, during which time the mixture had become very viscous. After cooling, the mixture was poured into 3 L of rapidly stirring DI water. The precipitated polymer was collected, washed with DI water (3×), torn into small pieces and dried at 50° C. until a constant weight was obtained.

Figure 9:
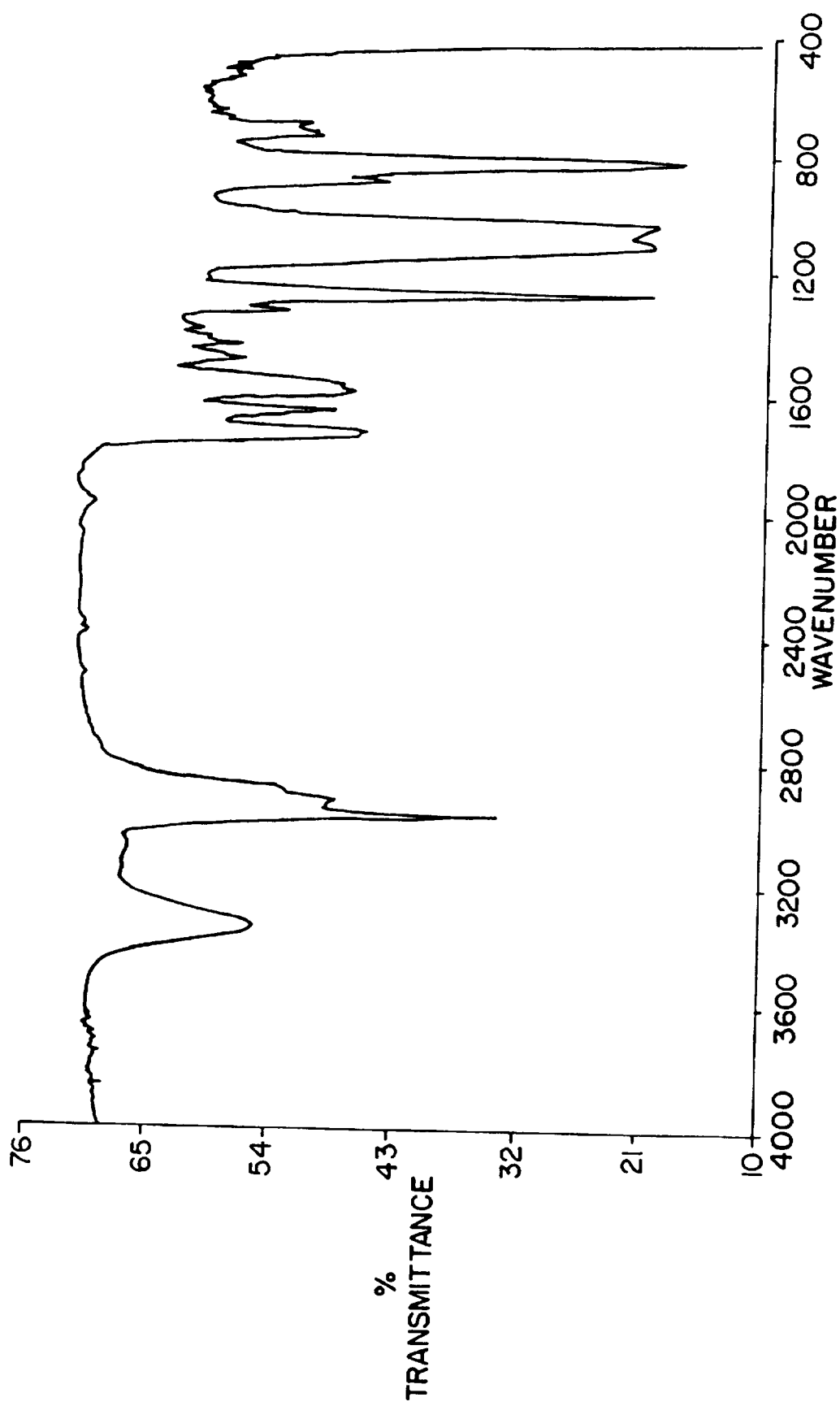
FIG. 9 is an infrared spectrum of a polyurea composition prepared in accordance with the present invention.

A membrane was prepared as described above. An infrared spectrum of the product was obtained and is reproduced in FIG. 9, exhibiting the expected absorbance bands ($cm^{-1}$).

EXAMPLE 3

This example provides the formulations and properties of representative membranes.

Table 1 provides the five formulations for representative polymers which were then formed into membranes. The polymers were prepared by solution polymerization.

TABLE 1

Representative Polymer Formulations

| Polymer | Diisocyanate | Poly(alkylene glycol) | Aliphatic diol | Siloxane |
|---|---|---|---|---|
| 1 | 1,6-Hexamethylene | PEG 600 (20%) | DEG (60%) | Aminopropyl (20%) |
| 2 | Isophorone | PEG 600 (20%) | DEG (50%) | Aminopropyl (30%) |
| 3 | 1,6-Hexamethylene | PEG 600 (50%) | None | Aminopropyl (50%) |
| 4 | 1,6-Hexamethylene | PEG 400 (40%) | None | Aminopropyl (60%) |
| 5 | 1,6-Hexamethylene | PEG 600 (60%) | None | Aminopropyl (40%) |

Table 2 provides certain physical and chemical properties of the polymers provided above.

TABLE 2

Physical Properties of Representative Polymers

| Polymer | Water Pickup (%) | $D_{oxygen}$ (× $10^{-6}$ $cm^2$/sec) | $D_{glucose}$ (× $10^{-9}$ $cm^2$/sec) |
|---|---|---|---|
| 1 | 28.5 | 1.21 | 18.5 |
| 2 | 31.3 | 0.57 | 55.7 |
| 3 | 44 | 1.50 | 105 |
| 4 | 57 | 1.22 | 13.5 |

TABLE 2-continued

Physical Properties of Representative Polymers

| Polymer | Water Pickup (%) | $D_{oxygen}$ (× $10^{-6}$ $cm^2$/sec) | $D_{glucose}$ (× $10^{-9}$ $cm^2$/sec) |
|---|---|---|---|
| 5 | 71 | 1.45 | 155 |

EXAMPLE 4

This example illustrates the evaluation of a membrane-coated biosensor constructed according to the present invention.

Figure 10A:
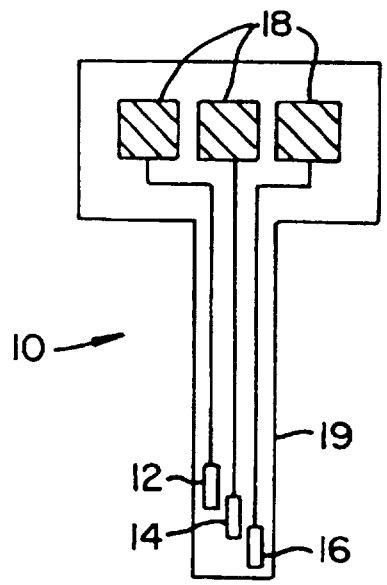
FIG. 10A is a schematic top view of a glucose sensor having electrodes covered with a polymer composition of the invention.
Figure 10B:
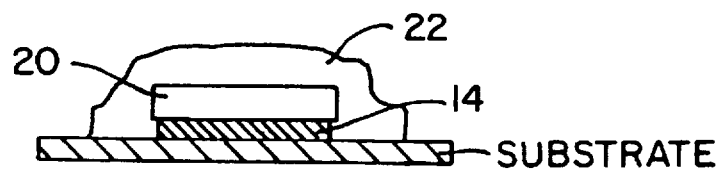
FIG. 10B is a sectional side view of a working electrode of the sensor which is covered with layers of an enzyme and a polymer composition of the invention.

A membrane prepared from the polymer identified as 3 above was found to have excellent mechanical properties as well as appropriate oxygen and glucose diffusivities. The membrane was evaluated using a prototype glucose sensor illustrated in FIG. 10A. According to FIG. 10A, a sensor 10 was constructed having a reference electrode 12, a working electrode 14, and a counter electrode 16 deposited on a polymeric sheet 19. A series of bonding pads 18 complete the sensor 10. As shown in FIG. 10B, the working electrode 14 was covered with a layer 20 of the enzyme glucose oxidase and the entire electrode array was coated with a layer 22 of the polymer 3 by dip coating two times from a 5 wt % solution of the polymer in THF. The sensor was connected to a commercial potentiostat (BAS Instruments, not shown) and operated with a potential of +0.6 volts between the working electrode and the reference electrode.

Figure 11:
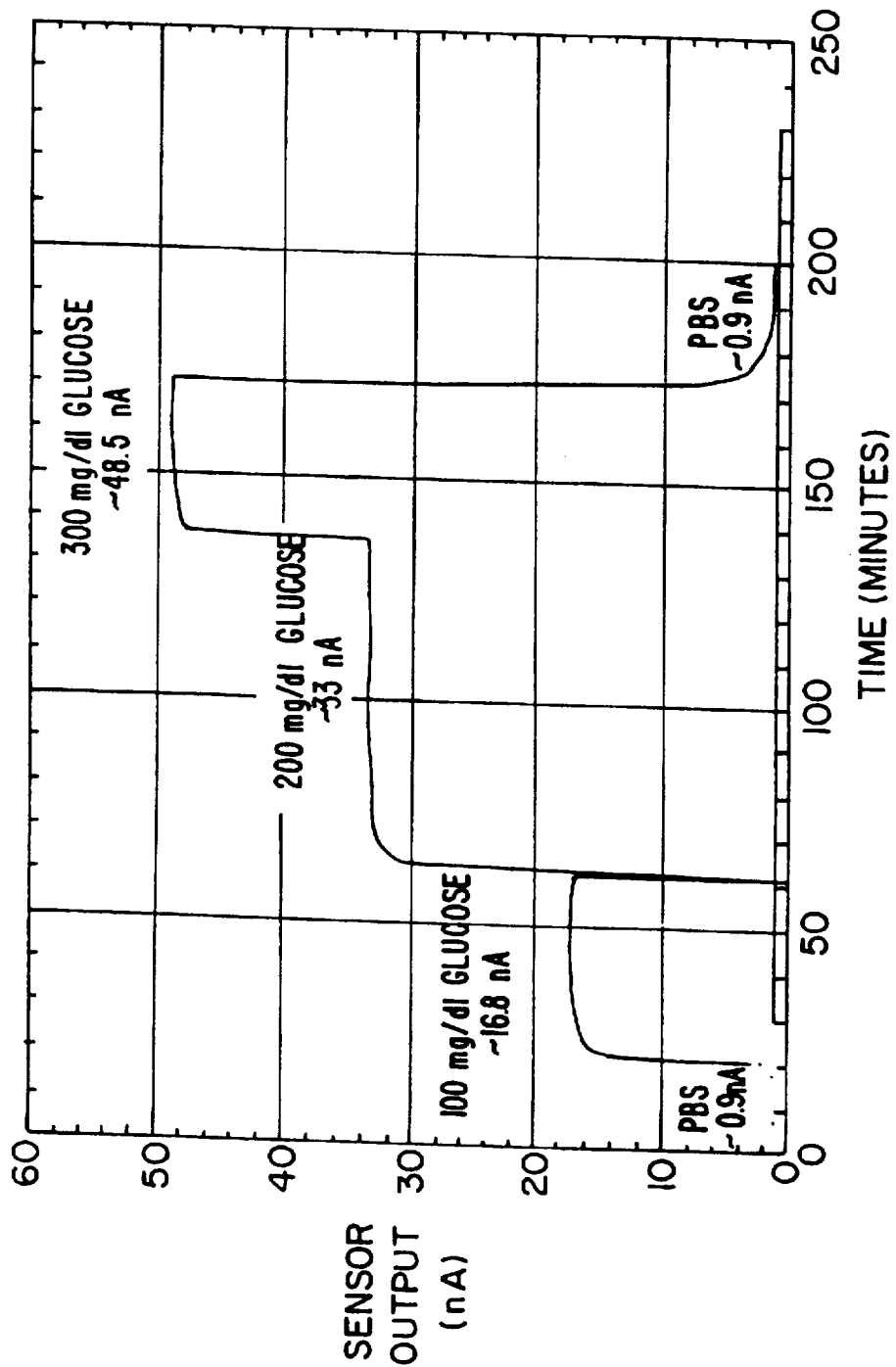
FIG. 11 is a graph showing sensor output in various glucose solutions as a function of time.

Glucose response is shown in FIG. 11. As seen in FIG. 11, the response of the electrode system is linear over the physiological glucose range, suggesting relative independence of local $O_2$ concentration. All of the other polymers tested showed similar behavior to the polymer identified as 3 and are acceptable as membranes for biosensor applications.

The above description is illustrative and not restrictive. Many variations of the invention will become apparent to those of skill in the art upon review of this disclosure. Merely by way of example a variety of solvents, membrane formation methods, and other materials may be used without departing from the scope of the invention. The scope of the invention should, therefore, be determined not with reference to the above description, but instead should be determined with reference to the appended claims along with their full scope of equivalents.

All publications, patents and patent applications mentioned in this specification are herein incorporated by reference into the specification to the same extent as if each individual publication, patent or patent application was specifically and individually indicated to be incorporated herein by reference.

What is claimed is:

1. A biocompatible membrane formed from a reaction mixture of:
   (a) a diisocyanate, said diisocyanate comprising about 50 mol % of the reactants in said mixture;
   (b) a hydrophilic polymer which is a member selected from the group consisting of a hydrophilic polymer diol, a hydrophilic polymer diamine and combinations thereof;
   (c) a siloxane polymer having functional groups at the chain termini, said membrane having a glucose diffusion coefficient of from about $1 \times 10^{-9}$ $cm^2$/sec to about $200 \times 10^{-9}$ $cm^2$/sec, a water pickup of at least 25% and a ratio of $D_{oxygen}/D_{glucose}$ of from about 5 to about 200

2. A biocompatible membrane in accordance with claim 1, wherein said functional groups are members selected from the group consisting of amino, hydroxyl and carboxylic acid.

3. A biocompatible membrane in accordance with claim 1, wherein said hydrophilic polymer is a poly(ethylene)glycol selected from the group consisting of PEG 200, PEG 400 and PEG 600.

4. A biocompatible membrane in accordance with claim 1, wherein said diisocyanate is a member selected from the group consisting of isophorone diisocyanate, 1,6-hexamethylene diisocyanate and 4,4'-methylenebis (cyclohexyl isocyanate).

5. A biocompatible membrane in accordance with claim 1, wherein said reaction mixture further comprises (d) a chain extender.

6. A biocompatible membrane in accordance with claim 5, wherein said chain extender is selected from the group consisting of an alkylene diol, an alkylene diamine, an aminoalkanol and combinations thereof.

7. A biocompatible membrane in accordance with claim 1, wherein said diisocyanate is 1,6-hexamethylene diisocyanate, said hydrophilic polymer is selected from the group consisting of PEG 400 and PEG 600 and is present in an amount of about 17 to about 32 mol %, and said siloxane polymer is aminopropyl polysiloxane having a molecular weight of about 2000 to about 4000 and is present in an amount of about 17 to about 32 mol %.

8. An implantable biosensor for measuring the reaction of an analyte and oxygen, said biosensor having a biocompatible membrane according to claim 1.

9. An implantable biosensor in accordance with claim 8, wherein the analyte comprises glucose.

* * * * *